US006641826B2

(12) United States Patent  (10) Patent No.: US 6,641,826 B2
Durden  (45) Date of Patent: Nov. 4, 2003

(54) WIPE WITH IMPROVED CLEANSING

(75) Inventor: Catherine Durden, Midland Park, NJ (US)

(73) Assignee: Playtex Products, Inc., Westport, CT (US)

( * ) Notice: Subject to any disclaimer, the term of this patent is extended or adjusted under 35 U.S.C. 154(b) by 82 days.

(21) Appl. No.: 09/891,637

(22) Filed: Jun. 26, 2001

(65) Prior Publication Data

US 2002/0061286 A1 May 23, 2002

Related U.S. Application Data

(60) Provisional application No. 60/214,650, filed on Jun. 26, 2000.

(51) Int. Cl.$^7$ .......................... A01N 25/34; A61K 7/06
(52) U.S. Cl. ................. 424/402; 424/70.1; 424/401
(58) Field of Search ........................ 424/401, 402, 424/70.1

(56) References Cited

U.S. PATENT DOCUMENTS

| 2,565,887 A | 8/1951 | Salfisberg ................. 206/56 |
| 3,414,927 A | 12/1968 | Worcester ............... 15/104.93 |
| 3,786,615 A | 1/1974 | Bauer ..................... 53/21 FC |
| 4,309,469 A | 1/1982 | Varona ..................... 428/74 |
| 4,383,986 A | 5/1983 | Dubash et al. ............. 424/25 |
| 4,692,374 A | 9/1987 | Bouchette ................. 428/288 |
| 4,732,797 A | 3/1988 | Johnson et al. ............ 428/74 |
| 4,737,405 A | 4/1988 | Bouchette ................. 428/288 |
| 4,741,944 A | 5/1988 | Jackson et al. ............ 428/152 |
| 4,772,501 A | 9/1988 | Johnson et al. ............ 428/74 |
| 4,781,974 A | 11/1988 | Bouchette et al. ......... 428/288 |
| 4,817,790 A | 4/1989 | Porat et al. ............... 206/205 |
| 4,818,594 A | 4/1989 | Albien et al. ............. 428/224 |
| 4,865,221 A | 9/1989 | Jackson et al. ............ 221/48 |
| 4,904,524 A | 2/1990 | Yoh ....................... 428/311.3 |
| 4,941,995 A | 7/1990 | Richards .................. 252/407 |
| 5,049,440 A | 9/1991 | Bornhoeft, III et al. .... 428/288 |
| 5,141,803 A | 8/1992 | Pregozen ................. 428/288 |
| 5,152,996 A | 10/1992 | Corey et al. .............. 424/443 |
| 5,215,759 A | 6/1993 | Mausner .................. 424/489 |
| 5,219,646 A | 6/1993 | Gallagher et al. ......... 428/287 |
| 5,256,417 A | 10/1993 | Koltisko ................... 424/402 |
| 5,439,682 A | 8/1995 | Wivell et al. ............. 724/401 |
| 5,507,968 A | 4/1996 | Palaikis ..................... 252/90 |
| 5,512,199 A | 4/1996 | Khan et al. ............... 252/106 |
| 5,585,104 A | * 12/1996 | Ha et al. .................. 424/401 |
| 5,599,549 A | 2/1997 | Wivell et al. ............. 424/401 |
| 5,629,081 A | * 5/1997 | Richards et al. ............ 442/96 |
| 5,635,469 A | 6/1997 | Fowler et al. ............. 510/406 |
| 5,648,083 A | 7/1997 | Blieszner et al. .......... 424/402 |
| 5,658,577 A | 8/1997 | Fowler et al. ............. 424/401 |
| 5,665,364 A | 9/1997 | McAtee et al. ............ 424/401 |
| 5,683,971 A | 11/1997 | Rose et al. ............... 510/130 |
| 5,686,088 A | 11/1997 | Mitra et al. .............. 424/404 |
| 5,686,089 A | 11/1997 | Mitra et al. .............. 424/405 |
| 5,699,912 A | 12/1997 | Ishikawa et al. ........... 206/494 |
| 5,702,992 A | 12/1997 | Martin et al. ............. 442/123 |
| 5,716,625 A | 2/1998 | Hahn et al. ............... 424/401 |
| 5,733,572 A | 3/1998 | Unger et al. .............. 424/450 |
| 5,736,128 A | 4/1998 | Chaudhuri et al. ........ 424/78.03 |
| 5,750,484 A | 5/1998 | Falbaum et al. ........... 510/276 |
| 5,753,245 A | 5/1998 | Fowler et al. ............. 424/401 |
| 5,753,246 A | 5/1998 | Peters .................... 424/404 |
| 5,804,203 A | 9/1998 | Hahn et al. .............. 424/401 |
| 5,908,617 A | 6/1999 | Moore et al. ............. 424/70.19 |
| 5,915,394 A | 6/1999 | Rickard ................... 132/333 |
| 5,939,050 A | 8/1999 | Iyer et al. .................. 424/49 |
| 5,942,214 A | 8/1999 | Lucas et al. ............... 424/65 |
| 5,962,399 A | 10/1999 | Wulff et al. .............. 510/470 |
| 5,968,539 A | 10/1999 | Beerse et al. ............. 424/405 |
| 5,993,792 A | 11/1999 | Rath et al. ............... 424/70.28 |
| 6,001,344 A | 12/1999 | Villa et al. .............. 424/78.02 |
| 6,007,799 A | 12/1999 | Lee et al. .................. 424/65 |
| 6,015,547 A | 1/2000 | Yam ........................ 424/49 |
| 6,015,816 A | 1/2000 | Kostyniak et al. ......... 514/299 |
| 6,033,679 A | 3/2000 | Woo et al. ............... 424/401 |
| 6,042,839 A | 3/2000 | Lahanas et al. ........... 424/401 |
| 6,048,836 A | 4/2000 | Romano et al. ........... 510/490 |

* cited by examiner

Primary Examiner—Thurman K. Page
Assistant Examiner—S. Howard
(74) Attorney, Agent, or Firm—Ohlandt, Greeley, Ruggiero & Perle, LLP

(57) ABSTRACT

The present invention relates to a liquid formulation for a baby wipe. The preferred formulation has cocamidopropyl betaine, and PEG-80 glyceryl cocoate/PEG-30 glyceryl cocoate.

23 Claims, No Drawings

WIPE WITH IMPROVED CLEANSING

This application claims the benefit of U.S. Provisional Application No. 60/214,650, filed Jun. 26, 2000, the contents of which are hereby incorporated by reference into this application.

BACKGROUND OF THE INVENTION

1. Field of the Invention

The present invention relates to a formulation for a wipe. More particularly, the present invention relates to a wipe or towelette formulation that has improved cleaning or cleansing ability. The wipe is particularly useful for cleaning a diaper area of a baby or an infant because of the mildness of the formulation.

2. Description of the Prior Art

A towelette or wipe is generally an absorbent sheet that is treated or pre-moistened with a liquid formulation. The liquid employed in pre-moistening the sheet is generally an aqueous solution. The solution may have a surface active detergent, a humectant and, in some instances, also a fragrance.

Typical baby wipe liquid formulations have water, propylene glycol, a mild surfactant, a lanolin derivative, one or more preservatives and other desired additives, such as a fragrance or botanical. Such formulations have an acceptable level of cleaning, with little consumer dissatisfaction. The pre-moistened towelette has its liquid work in conjunction with the fabric to cleanse the diaper area of urine and fecal matter. It is believed that the fabric, by virtue of being wet, is what contributes significantly to the cleansing ability of the towelette. In other words, the texture of the fabric or substrate contributes more to cleansing than the actual ingredients in the liquid. Heretofore, little emphasis has been placed on the combination of ingredients in the liquid to enhance the cleansing ability of a wipe, especially a baby or infant wipe.

For example, U.S. Pat. Nos. 4,741,944 and 4,865,221 to Jackson et al., provide wet wipes having a liquid in the sheet and/or web. The liquid includes water, benzalkonium chloride, citric acid, disodium phosphate, trisodium ethylene diamine tetraacetic acid, polyethylene glycol-75 lanolin, cocoamphocarboxyglycinate, propylene glycol, methylparaben, propylparaben, butylparaben, polysorbate 20 and fragrance. The Jackson et al. patents focus on an improved fabric that is interweaved in a manner so as to facilitate dispensing of each wipe from the container.

U.S. Pat. Nos. 4,732,797 and 4,772,501 to Johnson et al. are directed to a natural acid preservation system for a wet wipe that consists of citric acid and sorbic acid. U.S. Pat. No. 5,141,803 to Pregozen provides a nonwoven wipe impregnating composition. A specific cationic biocide is included in the preservative system. The cationic biocide, polyhexamethylene biguanide hydrochloride, allegedly greatly minimizes the slippery feel of the wet wipe.

U.S. Pat. No. 4,737,405 to Bouchette is directed to a binder catalyst for an antimicrobially active, non-woven web. Also, U.S. Pat. No. 4,781,974 to Bouchette et al. is directed to an antimicrobially active wet wipe having an antimicrobially active, non-woven web and a liquid containing a second antimicrobial agent. U.S. Pat. No. 5,512, 199 to Khan et al. is directed to a hand wipe that includes an alcohol, an antimicrobial agent, a water soluble polymer, a polyalkylene glycol and a moisturizer and/or emollient, along with water.

Also, U.S. Pat. No. 5,152,996 to Corey et al. is directed to a nonwoven wipe impregnated with an aqueous solution of a zinc acetate peroxide and a surfactant.

U.S. Pat. No. 5,256,417 to Koltisko is directed to a water dispersible towelette impregnated with non-aqueous lotion formulations. The towelette was made of nonwoven fibers coated or impregnated with a polyvinyl alcohol or an emulsion polymer binder to impart wet strength.

U.S. Pat. No. 5,648,083 to Blieszner et al. is directed to a wet wipe that has silicone oil and a polymeric emulsifier.

U.S. Pat. No. 5,753,246 to Peters is directed to a packaged germicidal towelette that has aloe vera and cocoa butter, as well as a chlorhexidine alcohol solution.

The present invention is a liquid wipe formulation that has surprisingly better cleansing ability than a typical liquid wipe formulation when used on the same fabric or substrate. The surprisingly better cleansing ability is achieved by the unique combination of surfactants found in the subject wipe, preferably a baby wipe. Also, the present liquid wipe formulation has the same or increased mildness than the typical liquid wipe formulations. Still further, the present formulation does not cause skin irritation.

SUMMARY OF THE INVENTION

It is an object of the present invention to provide a liquid wipe formulation that has improved cleansing ability.

It is another object of the present invention to provide such a wipe formulation that is mild and, thus, conducive for use in a baby or an infant wipe.

It is still another object of the present invention to provide such a wipe formulation that has a unique combination of cleansing agents.

It is yet another object of the present invention to provide such a wipe formulation in which the unique combination of cleansing agents is at least 0.20 percent by weight of the total weight of the composition.

It is a further object of the present invention to provide such a wipe formulation in which the cleansing agents may include either (1) cocamidopropyl betaine, or (2) PEG-80 glyceryl cocoate and PEG-30 glyceryl cocoate, but has been found that the combination of both has enhanced cleansing ability.

These and other objects of the present invention are achieved by the present invention that is a liquid or aqueous wipe composition comprising two cleansing agents, namely cocamidopropyl betaine, and PEG-80 glyceryl cocoate/ PEG-30 glyceryl cocoate. The composition may further include a solvent, such as water, a humectant, a fragrance, a skin conditioning agent, a preservative, a chelating agent, a salt, and/or a pH adjuster.

DETAILED DESCRIPTION OF THE INVENTION

The present invention is a liquid wipe formulation used primarily in a baby or infant wipe. The combination of two cleansing agents has been found to have a surprisingly unexpected cleaning ability, especially for urine and fecal matter.

The first cleansing agent is cocamidopropyl betaine. This ingredient also acts as a skin conditioning agent. In the present invention, the cocamidopropyl betaine is present in an amount up to about 0.25 wt % of the total weight of the liquid composition. Preferably, it is in an amount about 0.15 wt %.

The second cleansing agent is a glyceryl cocoate having the formula:

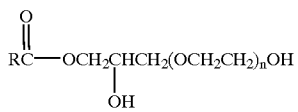

where R represents a coconut fatty radical and n has a value from 20 to 100. The preferred second cleansing agent is a mixture of glyceryl cocoate wherein n is 30 and 80 (PEG-30 glyceryl cocoate and PEG-80 glyceryl cocoate respectively). In the present invention, this second cleansing agent is present in an amount up to about 0.25 wt % of the total weight of the liquid composition. Preferably, it is present in an amount about 0.15 wt %.

The first and second cleansing agents are known as surfactants.

It is believed that either one of the above-described cleansing agents alone may improve cleansing ability. It is also believed that the first cleansing agent (cocamidopropyl betaine) may be added to either component of the second cleansing agent (PEG-80 glyceryl cocoate or PEG-30 glyceryl cocoate) to improve cleansing ability.

Besides the two cleansing agents, additional cleansing agents may be used in the present composition. For example, disodium cocoamphodiacetate may be present in an amount up to about 0.10 wt % of the total weight of the liquid composition. Also, decyl polyglucose may be present in addition to or instead of the disodium cocoamphodiacetate, and in an amount up to about 0.10 wt %. Again, these additional cleansing agents may be surfactants.

The total surfactants, namely disodium cocoamphodiacetate, cocamidopropyl betaine, PEG-80 glyceryl cocoate/PEG-30 glyceryl cocoate, and decyl polyglucose, must be a minimum of about 0.20 wt % of the total weight of the liquid composition.

Besides the cleansing agents discussed above, the present composition may include one or more of the following: a solvent, a humectant, a fragrance, a skin conditioning agent, a preservative, a chelating agent, a salt and/or a pH adjuster.

The preferred solvent is water. Water is preferably present in an amount from about 50 wt % to about 98 wt % of the total weight of the liquid composition.

The humectant is preferably one or more of the following: glycerol, propylene glycol, sorbitol urea, amino acids, certain polyols and other compounds with hygroscopic properties. The preferred humectant is propylene glycol. The humectant is preferably present in an amount from about 0.10 wt % up to about 1 wt % of the total weight of the liquid composition. More preferably, the humectant is present in an amount about 0.50 wt %.

The composition may include a fragrance. Any conventional fragrance that does not adversely affect an infant or baby may be used. Preferably, the fragrance is present in an amount from about 0 wt % up to about 0.20 wt %, and more preferably about 0.05 wt % of the total weight of the liquid composition.

The skin conditioning agent is preferably one or more of the following: botanical extracts including aloe vera gel, esters including tocopherol acetate, quaternary ammonium compounds, asymmetrical carbonates, N-substituted carboxamides, ureas or phosphine oxides, and organic salts. The preferred skin conditioning agent is aloe vera gel. The skin conditioning agent is preferably present in an amount from about 0 wt % up to about 1 wt % of the total weight of the liquid composition. More preferably, it is present in an amount about 0.01 wt %.

The preservative is preferably one or more of the following: sodium hydroxymethylglycinate, polyaminopropyl biguanide, quaternary ammonium compounds, EDTA salts, EDTA fatty acid conjugates, alkanols especially ethanol, isopropyl alcohol, benzyl alcohol, parabens, sorbates, urea derivatives, and isothiazolinone, or mixtures thereof. The preferred preservative is sodium hydroxymethylglycinate. The preservative is preferably present in an amount from about 0.5 wt % to about 2 wt % of the weight of the liquid composition, and more preferably about 0.5 wt %.

The chelating agent is preferably one or more of the following: disodium EDTA (ethylenediamine tetraacetate), ethylene-diamine-tetra-acetic acid (ethylenedioxy)-diethylene-dinitrilo-tetra-acetic acid, salicylaldoxime, quinolinol, triethylenetetramine, or mixtures thereof. The preferred chelating agent is disodium EDTA. The chelating agent is preferably present in an amount from about 0 wt % up to about 0.2 wt % of the total weight of the liquid composition. More preferably, the chelating agent is present in an amount about 0.10 wt %.

The salt is preferably potassium sorbate or any organic acid such as malic acid or benzoic acid. Potassium sorbate also acts as a preservative. Preferably, it is present in an amount about 0.10 wt % to about 0.30 wt %, and more preferably about 0.14 wt % of the total weight of the liquid composition.

The preferred pH adjuster is citric acid. Preferably, citric acid is present in an amount from about 0.10 wt % to about 0.30 wt % of the total weight of the liquid composition. More preferably, the citric acid is present in an amount about 0.20 wt %.

Thus, a preferred composition according to the present invention is a baby or infant wipe composition comprising: water; and cocamidopropyl betaine and PEG-80 glyceryl cocoate/PEG-30 glyceryl cocoate, each in an amount from about 0 wt % to about 0.25 wt %, with the total amount being at least about 0.20 wt % of the total weight of the liquid composition. The composition may also include propylene glycol in an amount from about 0.1 wt % up to about 1 wt %; fragrance in an amount from about 0 wt % up to about 0.20 wt %; and/or aloe vera gel in an amount from about 0 wt % up to about 1 wt %. Yet further, the composition may include disodium EDTA in an amount about 0 wt % up to about 0.20 wt %; and potassium sorbate in an amount from about 0.10 wt % to about 0.30 wt %, both of which act or have preservative properties and, optionally, citric acid in an amount about 0.10 wt % to about 0.30 wt % of the total weight of the liquid composition.

The subject liquid composition is listed in Table 1 in weight percents, along with a conventional formulation. This conventional formulation is used in the two experiments discussed below.

TABLE 1

| Ingredient | Conventional formulation (wt %) | Subject Composition (wt %) | Ranges* (wt %) |
|---|---|---|---|
| Water | QS | QS | QS |
| Disodium cocoamphodiacetate | 0.10 | — | Up to 0.10 |
| PEG-60 Lanolin | 0.10 | — | — |
| Cocamidopropyl Betaine | — | 0.15 | Up to 0.25 |
| PEG-80 Glyceryl cocoate (and) PEG-30 Glyceryl cocoate | — | 0.15 | Up to 0.25 |

TABLE 1-continued

| Ingredient | Conventional formulation (wt %) | Subject Composition (wt %) | Ranges* (wt %) |
|---|---|---|---|
| Decyl Polyglucose | — | — | Up to 0.10 |
| Propylene glycol | 0.50 | 0.50 | Up to 0.10 |
| Fragrance | 0.05 | 0.05 | Up to 0.20 |
| Aloe Vera Gel | 0.01 | 0.01 | Up to 1.00 |
| Preservative | 0.50 | 0.50 | 0.50 to 2 |
| Disodium EDTA | 0.10 | 0.10 | Up to 0.20 |
| Potassium sorbate | 0.14 | 0.14 | 0.10 to 0.30 |
| Citric acid | 0.10 | 0.20 | 0.10 to 0.30 |
| Total | 100.00 | 100.00 | 100.00 |

*The total surfactant (disodium cocoamphodiacetate, cocamidopropyl betaine, PEG-80 glyceryl cocoate/PEG-30 glyceryl cocoate, and decyl polyglucose) must be a minimum of 0.20%.

EXPERIMENTS

A skin irritation and sensitization test was performed on the present formulation using 200 subjects. No subjects developed an adverse reaction.

Two Experiments were performed to compare the performance of the subject composition with both a conventional formulation and were questioned comparing both to the brand used most often by the panelists (either Brand A or Brand B).

The wipes for the conventional formulation and the improved cleansing subject composition are composed of 65 grams per square meter embossed, non-woven fabric. The conventional wipe had the conventional formulation recited above. The subject wipe had the subject composition recited above.

The difference between the two experiments is the labeling of the subject wipe. The wipes with the subject composition were distributed to panelists using different labels (hereinafter, "Wipe with Subject Composition" in the first experiment) and ("Subject Composition Wipe" in the second experiment) in an attempt to unbias name recognition.

For each experiment, there were fifty (50) panelists with children under three. Each panelist used each wipe (the conventional formulation and subject formulation) for one week. The panel was evenly split by the two brands panelists used most often, that is between Brand A users and Brand B users.

TABLE 2

Experiment 1

| Selected Properties | Conventional Wipe | Wipe with Subject Composition | Brand used most often |
|---|---|---|---|
| Overall Preference | 34% | 66%*** | N/A |
| Total positive purchase intent | 57% | 76% | N/A |
| Smells good | 10% | 62% | 12% |
| Thick | 16% | 26% | 20% |
| Cottony soft | 8% | 22% | 22% |
| Gentle | 8% | 34% | 12% |
| Durable | 8% | 18% | 18% |
| Leaves no soapy residue | 38% | 18% | 14% |
| Easy to pick up one at a time | 22% | 18% | 22% |
| Cleans effectively | 14% | 38% | 14% |

TABLE 3

Experiment 2

| Selected Properties | Conventional Wipe | Subject Composition Wipe | Brand used most often |
|---|---|---|---|
| Overall Preference | 33% | 67%*** | N/A |
| Total positive purchase intent | 56% | 74% | N/A |
| Smells good | 10% | 62% | 12% |
| Thick | 16% | 26% | 16% |
| Cottony soft | 12% | 24% | 18% |
| Gentle | 12% | 34% | 10% |
| Durable | 10% | 22% | 16% |
| Leaves no soapy residue | 42% | 18% | 14% |
| Easy to pick up one at a time | 20% | 30% | 14% |
| Cleans effectively | 20% | 40% | 3% |

*** = greater than 95% confidence limit
Note: totals do not equal 100 because of mixed replies by panelists

TABLE 4

Preference Summary

| Brand used (% of panel) | Experiment 1 (Brand A 48%/ Brand B 52%) | | Experiment 2 (Brand A 50%/ Brand B 50%) | |
|---|---|---|---|---|
| | Preferred Conventional Wipe | Preferred with Wipe Subject Composition | Preferred Conventional Wipe | Preferred Subject Composition Wipe |
| Brand A | 23% | 25% | 18% | 32% |
| Brand B | 10% | 42% | 22% | 28% |

The results for each test were almost identical, regardless of the concept or labels, the panelist received. In both tests, the wipes with the subject composition were significantly preferred over the conventional wipe and the brand used most often by the panelists. The Preference Summary breaks down the wipe preference by the brands previously used by the consumers (Brand A and Brand B). The Preference Summary also shows a significant difference favoring the wipe with the subject composition in both Brand A and Brand B users.

The results from this test confirm that wipes with the subject composition were preferred over both the selected conventional wipe and the panelist's current brand. The consumers' preference for the improved cleansing formula is surprising for two reasons. First, the conventional formula and the present composition were tested using the same fabric substrate. The actual differences between the conventional formulation and the composition of the present invention are small. Therefore, the consumer is perceiving only differences between the liquid formulations. Thus, the unique cleansing agents in the present composition lead to a dramatic change in consumer preference for cleansing ability. Also of note is the mildness and gentleness that the present wipe maintains, in order to compete and be chosen over the conventional wipes and brand used most often by panelists.

Second, the consumer also perceives difference between the improved cleansing and the commercial wipe, which is the brand the consumer normally uses as shown in Table 4. Also, Tables 2 and 3 show that the improved cleansing wipe was preferred over both the conventional wipe and the brand that the consumer normally uses. In this case, the consumer's normal wipe (either Brand A or Brand B) has a different texture than the present wipe, and yet the consumer perceived the present wipe as the better cleaner. This is unusual because texture is generally considered to be the primary contributor to cleansing ability.

Thus, the present invention has been proven to be a superior cleansing composition to conventional formulations that are currently commercially available. The inclusion of surfactants such as cocamidopropyl betaine, and PEG-80 glyceryl cocoate/PEG-30 glyceryl cocoate, surprisingly improves cleansing ability. The two experiments clearly show evidence of a preference in a particular liquid formulation over another. The experiments also show that consumers prefer the subject liquid composition to the consumer's usual brand. The significance of consumer preference for a particular wipe due to the liquid formulation is a breakthrough in towelette development.

It should be understood that the foregoing description is only illustrative of the present invention. Various alternatives and modifications can be devised by those skilled in the art without departing from the invention. Accordingly, the present invention is intended to embrace all such alternatives, modifications and variances which fall within the scope of the appended claims.

What is claimed is:

1. A premoistened wipe having a cleansing composition comprising:

cocamidopropyl betaine; and

PEG-80 glyceryl cocoate/PEG-30 glyceryl cocoate, wherein the cocamidopropyl betaine is present in an amount from about 0 wt % up to about 0.25 wt % of the total weight of the composition, and wherein the PEG-80 glyceryl cocoate/PEG-30 glyceryl cocoate is present in an amount from about 0 wt % up to about 0.25 wt % of the total weight of the composition.

2. The composition of claim 1, wherein said cocamidopropyl betaine is present in an amount about 0.15 wt % of the total weight of the composition.

3. The composition of claim 1, wherein said PEG-80 glyceryl cocoate/PEG-30 glyceryl cocoate is present in an amount about 0.15 wt % of the total weight of the composition.

4. The composition of claim 1, wherein said cocamidopropyl betaine and said PEG-80 glyceryl cocoate/PEG-30 glyceryl cocoate is at least 0.20 wt % of the total weight of the composition.

5. The composition of claim 1, further comprising a solvent.

6. The composition of claim 1, further comprising a humectant.

7. The composition of claim 6, wherein said humectant is present in an amount from about 0.10 wt % to about 1 wt % of the total weight of the composition.

8. The composition of claim 1, further comprising a skin conditioning agent.

9. The composition of claim 8, wherein said skin conditioning agent is aloe vera gel.

10. The composition of claim 8, wherein the skin conditioning agent is in an amount from about 0 wt % up to about 1 wt % of the total weight of the composition.

11. The composition of claim 1, further comprising a preservative.

12. The composition of claim 11, wherein said preservative is sodium hydroxymethylglycinate.

13. The composition of claim 11, wherein said preservative is in an amount from about 0.5 wt % to about 2 wt % of the total weight of the composition.

14. The composition of claim 1, further comprising a pH adjuster.

15. The composition of claim 14, wherein said pH adjuster is in an amount from 0.10 wt % to 0.30 wt % of the total weight of the composition.

16. The composition of claim 1, further comprising a chelating agent.

17. The composition of claim 16, wherein said chelating agent is in an amount from about 0 wt % up to about 0.2 wt % of the total weight of the composition.

18. The composition of claim 1, further comprising a fragrance.

19. A premoistened wipe having a cleansing composition comprising cocamidopropyl betaine, wherein the cocamidopropyl betaine is present in an amount from about 0 wt % up to about 0.25 wt % of the total weight of the composition.

20. The composition of claim 19, further comprising glyceryl cocoate having the formula:

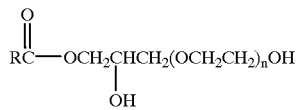

wherein R represents a coconut fatty radical and n has a value from 20 to 100.

21. The composition of claim 19, further comprising PEG-80 glyceryl cocoate.

22. The composition of claim 19, further comprising PEG 30 glyceryl cocoate.

23. A premoistened wipe having a cleansing composition comprising PEG-80 glyceryl cocoate and PEG-30 glyceryl cocoate, wherein the PEG-80 glyceryl cocoate and PEG-30 glyceryl cocoate are present in an amount from about 0 wt % up to about 0.25 wt % of the total weight of the composition.

* * * * *